(12) United States Patent
Kingsley et al.

(10) Patent No.: US 11,737,844 B2
(45) Date of Patent: Aug. 29, 2023

(54) END EFFECTOR ASSEMBLY FOR USE IN A ROBOTIC SURGICAL INSTRUMENT

(71) Applicant: Covidien LP, Mansfield, MA (US)

(72) Inventors: Dylan R. Kingsley, Broomfield, CO (US); Crystal A. Adams, Westminster, CO (US); Jason G. Weihe, Longmont, CO (US); William R. Whitney, Boulder, CO (US); Russell W. Holbrook, Longmont, CO (US); Zachary S. Heiliger, Nederland, CO (US); Curtis M. Siebenaller, Frederick, CO (US)

(73) Assignee: Covidien LP, Mansfield, MA (US)

( * ) Notice: Subject to any disclaimer, the term of this patent is extended or adjusted under 35 U.S.C. 154(b) by 395 days.

(21) Appl. No.: 16/997,139

(22) Filed: Aug. 19, 2020

(65) Prior Publication Data
US 2022/0054210 A1 Feb. 24, 2022

(51) Int. Cl.
| | | |
|---|---|---|
| *A61B 34/00* | (2016.01) | |
| *B25J 15/02* | (2006.01) | |
| *B25J 15/00* | (2006.01) | |
| *A61B 34/35* | (2016.01) | |

(52) U.S. Cl.
CPC .............. *A61B 34/70* (2016.02); *A61B 34/35* (2016.02); *B25J 15/009* (2013.01); *B25J 15/0028* (2013.01); *B25J 15/0226* (2013.01)

(58) Field of Classification Search
CPC . A61B 34/70; A61B 34/35; A61B 2017/2933; A61B 2017/2934; A61B 2017/2936; A61B 17/29; B25J 15/0028; B25J 15/009; B25J 15/0226
See application file for complete search history.

(56) References Cited

U.S. PATENT DOCUMENTS

| | | | | |
|---|---|---|---|---|
| 5,238,002 A | * | 8/1993 | Devlin | A61B 10/06 606/205 |
| 5,700,276 A | * | 12/1997 | Benecke | A61B 17/1608 606/208 |
| 5,752,973 A | | 5/1998 | Kieturakis | |
| 5,792,135 A | | 8/1998 | Madhani et al. | |
| 5,848,986 A | | 12/1998 | Lundquist et al. | |
| 6,309,397 B1 | * | 10/2001 | Julian | A61B 34/30 128/898 |
| 6,817,974 B2 | | 11/2004 | Cooper et al. | |
| 7,799,028 B2 | | 9/2010 | Schechter et al. | |
| 7,861,906 B2 | | 1/2011 | Doll et al. | |

(Continued)

FOREIGN PATENT DOCUMENTS

WO 2017136710 A2 8/2017

OTHER PUBLICATIONS

International Search Report and written opinion dated Dec. 6, 2021, issued in corresponding international application No. PCT/US2021/046462, 11 pages.

(Continued)

*Primary Examiner* — Julian W Woo
(74) *Attorney, Agent, or Firm* — Carter, DeLuca & Farrell LLP

(57) ABSTRACT

An end effector assembly of a robotic surgical instrument includes a clevis, first and second jaw members supported by the clevis, and a cam bar configured to move the first and second jaw members between an open state and a closed state.

20 Claims, 7 Drawing Sheets

(56) References Cited

U.S. PATENT DOCUMENTS

| | | | |
|---|---|---|---|
| 7,918,230 | B2 | 4/2011 | Whitman et al. |
| 8,469,991 | B2 * | 6/2013 | Kerr .................. A61B 18/1445 |
| | | | 606/205 |
| 8,579,176 | B2 | 11/2013 | Smith et al. |
| 9,055,961 | B2 | 6/2015 | Manzo et al. |
| 9,168,050 | B1 * | 10/2015 | Peine ................. A61B 17/2816 |
| 9,474,569 | B2 | 10/2016 | Manzo et al. |
| 2002/0099371 | A1 | 7/2002 | Schulze et al. |
| 2002/0177842 | A1 | 11/2002 | Weiss |
| 2003/0125734 | A1 | 7/2003 | Mollenauer |
| 2003/0208186 | A1 | 11/2003 | Moreyra |
| 2006/0022015 | A1 | 2/2006 | Shelton et al. |
| 2006/0025811 | A1 | 2/2006 | Shelton |
| 2007/0233052 | A1 | 10/2007 | Brock |
| 2007/0282358 | A1 | 12/2007 | Remiszewski et al. |
| 2008/0015631 | A1 | 1/2008 | Lee et al. |
| 2010/0274265 | A1 | 10/2010 | Wingardner et al. |
| 2010/0292691 | A1 | 11/2010 | Brogna |
| 2011/0118707 | A1 | 5/2011 | Burbank |
| 2011/0118708 | A1 | 5/2011 | Burbank et al. |
| 2011/0118709 | A1 | 5/2011 | Burbank |
| 2011/0118754 | A1 | 5/2011 | Dachs, II et al. |
| 2014/0012290 | A1 | 1/2014 | Cooper et al. |
| 2016/0066982 | A1 | 3/2016 | Marczyk et al. |
| 2017/0020543 | A1 | 1/2017 | Soni |
| 2018/0132925 | A1 | 5/2018 | Allen, IV et al. |

OTHER PUBLICATIONS

International Preliminary Report on Patentability and Written Opinion issued in corresponding International Application No. PCT/US2021/046462 dated Mar. 2, 2023, 9 pages.

* cited by examiner

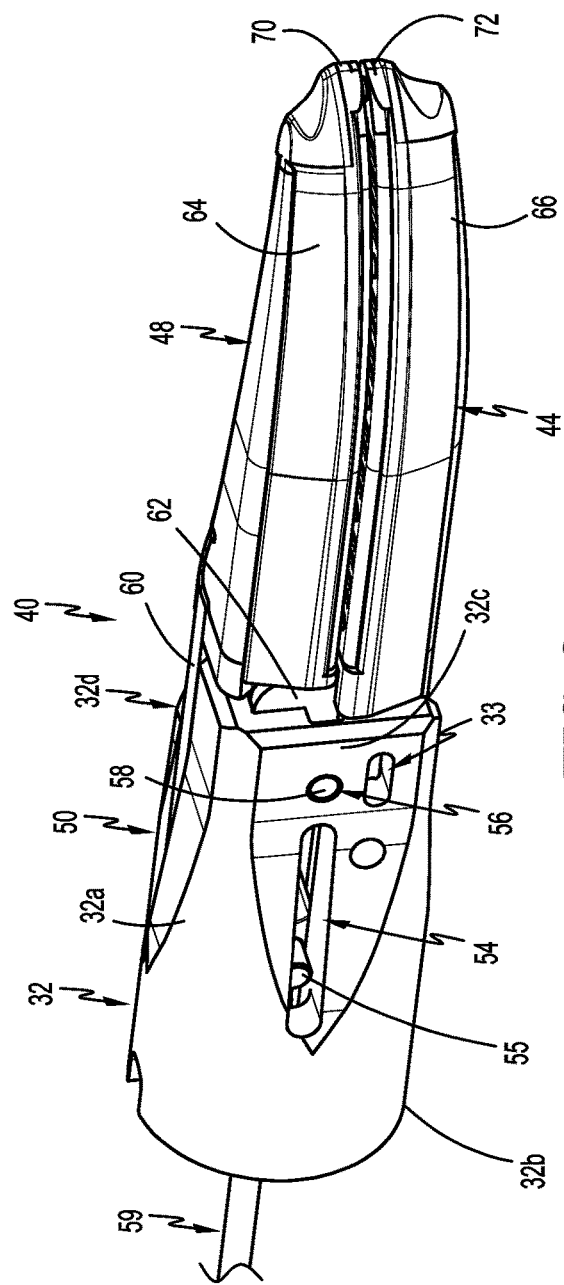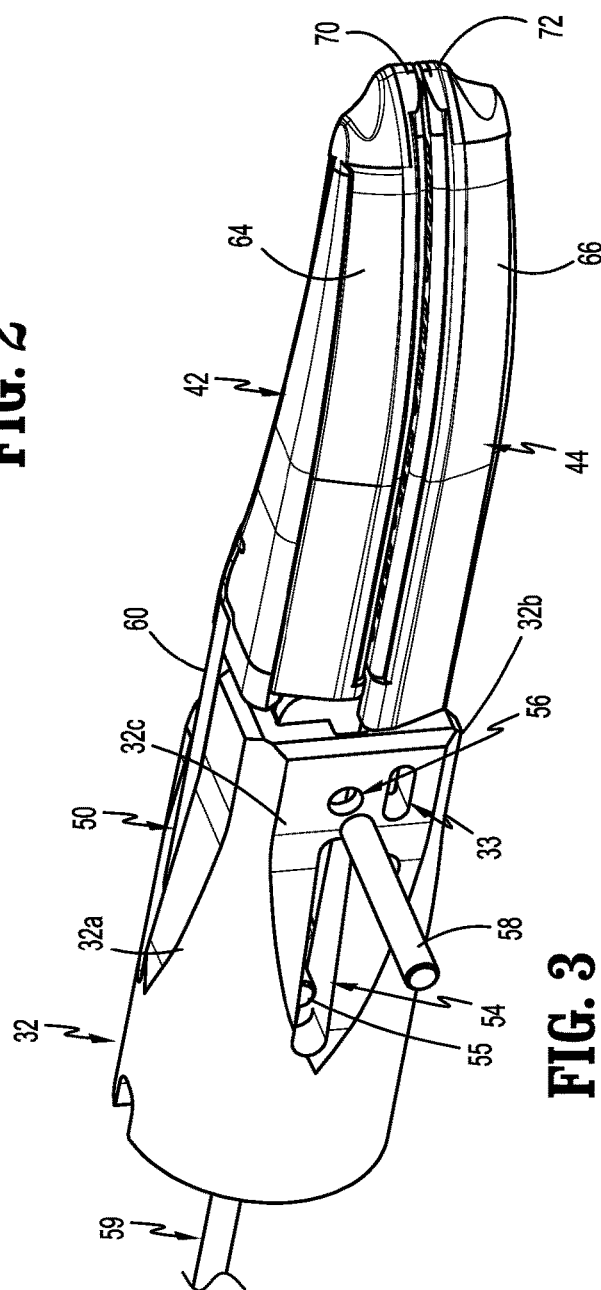

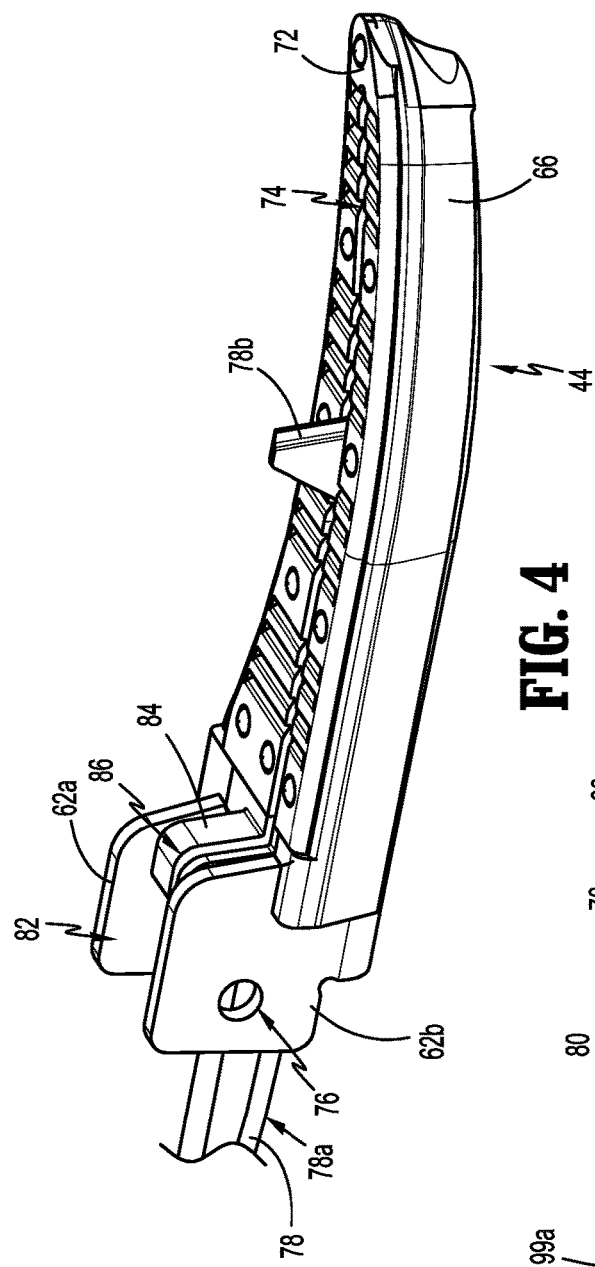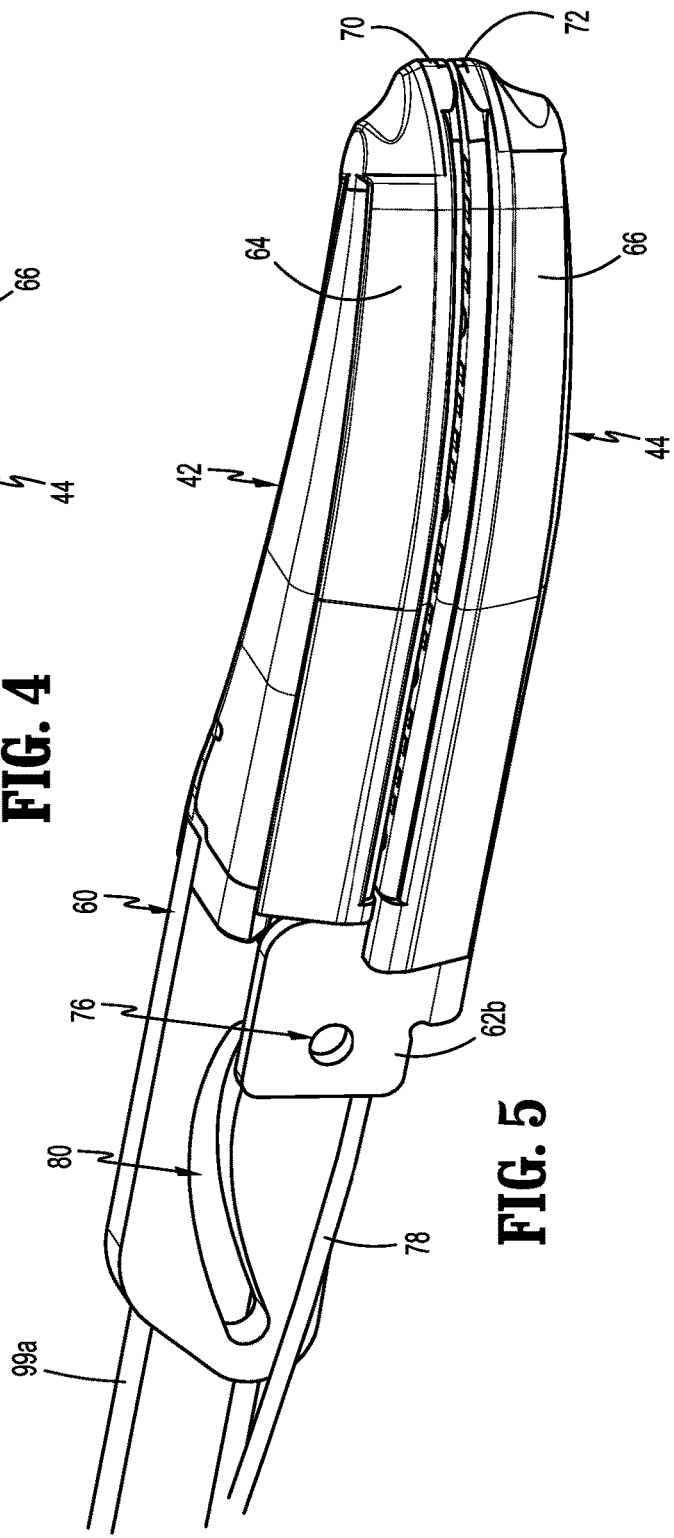
FIG. 4
FIG. 5

END EFFECTOR ASSEMBLY FOR USE IN A ROBOTIC SURGICAL INSTRUMENT

FIELD

The present disclosure relates to surgical instruments and, more specifically, to articulating end effector assemblies for use in robotic surgical systems.

BACKGROUND

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

The surgical instruments or portions thereof may be configured as single-use instruments or portions that are discarded after use, or may be configured as reusable instruments or portions that are cleaned and sterilized between uses. Regardless of the configurations of the surgical instruments, the console and robotic arm are capital equipment configured for long-term, repeated use. The console and robotic arm may be protected by a sterile barrier during use and/or wiped clean after use to ensure cleanliness for subsequent uses.

SUMMARY

As used herein, the term "distal" refers to the portion that is being described which is further from an operator (whether a human surgeon or a surgical robot), while the term "proximal" refers to the portion that is being described which is closer to the operator. The terms "about," "substantially," and the like, as utilized herein, are meant to account for manufacturing, material, environmental, use, and/or measurement tolerances and variations, and in any event may encompass differences of up to 10%. To the extent consistent, any of the aspects described herein may be used in conjunction with any or all of the other aspects described herein.

Provided in accordance with aspects of the present disclosure is an end effector assembly of a robotic surgical instrument. The end effector assembly includes a clevis, a first jaw member pivotably coupled to the clevis via a pivot pin, a second jaw member coupled to the clevis, and a cam bar having a distal end portion received within the clevis. The first jaw member defines a cam slot, and the distal end portion of the cam bar has a cam pin received in the cam slot. The distal end portion of the cam bar defines a cutout therein. The cam bar is configured to move through the clevis, whereby the cam pin of the cam bar pivots at least one of the first or second jaw members relative to the clevis between a closed state in which the first and second jaw members are closer to one another, and an open state in which the first and second jaw members are further apart from one another.

In aspects, the distal end portion of the cam bar may be configured to move between a distal position, in which the first and second jaw members are in the open state, and a proximal position, in which the first and second jaw members are in the closed state.

In aspects, the pivot pin may be configured to be received in the cutout of the distal end portion of the cam bar when the distal end portion of the cam bar is in the distal position.

In aspects, the distal end portion of the cam bar may include a cam block and the cam pin. The cam bar may define the cutout therein, and the cam pin may extend laterally outward from at least a first lateral side of the cam block.

In aspects, the cutout may have an annular shape.

In aspects, the cam block may have a distal-facing surface, and the cutout may be formed in the distal-facing surface.

In aspects, the clevis may have a side wall defining a linear slot, and the cam pin of the cam bar may be received in the linear slot.

In aspects, the first jaw member may include a distal body portion, and a proximal flange portion extending proximally from the distal body portion. The proximal flange portion may define the cam slot therein.

In aspects, the clevis may define an opening having the pivot pin received therein. The opening may be disposed distally of the linear slot.

In accordance with another aspect of the disclosure, a robotic surgical instrument is provided and includes a housing configured to be operably coupled to a surgical robotic arm, a shaft assembly extending distally from the housing, and an end effector assembly. The end effector assembly includes a clevis coupled to a distal end portion of the shaft assembly and configured to articulate relative thereto, a first jaw member pivotably coupled to the clevis via a pivot pin, a second jaw member coupled to the clevis, and a cam bar having a distal end portion received within the clevis. The first jaw member defines a cam slot, and the distal end portion of the cam bar has a cam pin received in the cam slot. The distal end portion of the cam bar defines a cutout therein. The cam bar is configured to move through the clevis, whereby the cam pin of the cam bar pivots at least one of the first or second jaw members relative to the clevis between a closed state in which the first and second jaw members are closer to one another, and an open state in which the first and second jaw members are further apart from one another.

BRIEF DESCRIPTION OF THE DRAWINGS

Various aspects and features of the present disclosure are described hereinbelow with reference to the drawings wherein:

FIG. 2 is a side perspective view illustrating an end effector assembly of the surgical instrument of FIG. 1;

FIG. 3 is a side perspective view of the end effector assembly of FIG. 2 illustrating a pivot pin separated from the end effector assembly;

FIG. 4 is a side perspective view illustrating a jaw member and a knife blade of the end effector assembly of FIG. 2;

FIG. 5 is a side perspective view illustrating first and second jaw members of the end effector assembly of FIG. 2;

DETAILED DESCRIPTION

Figure 1:
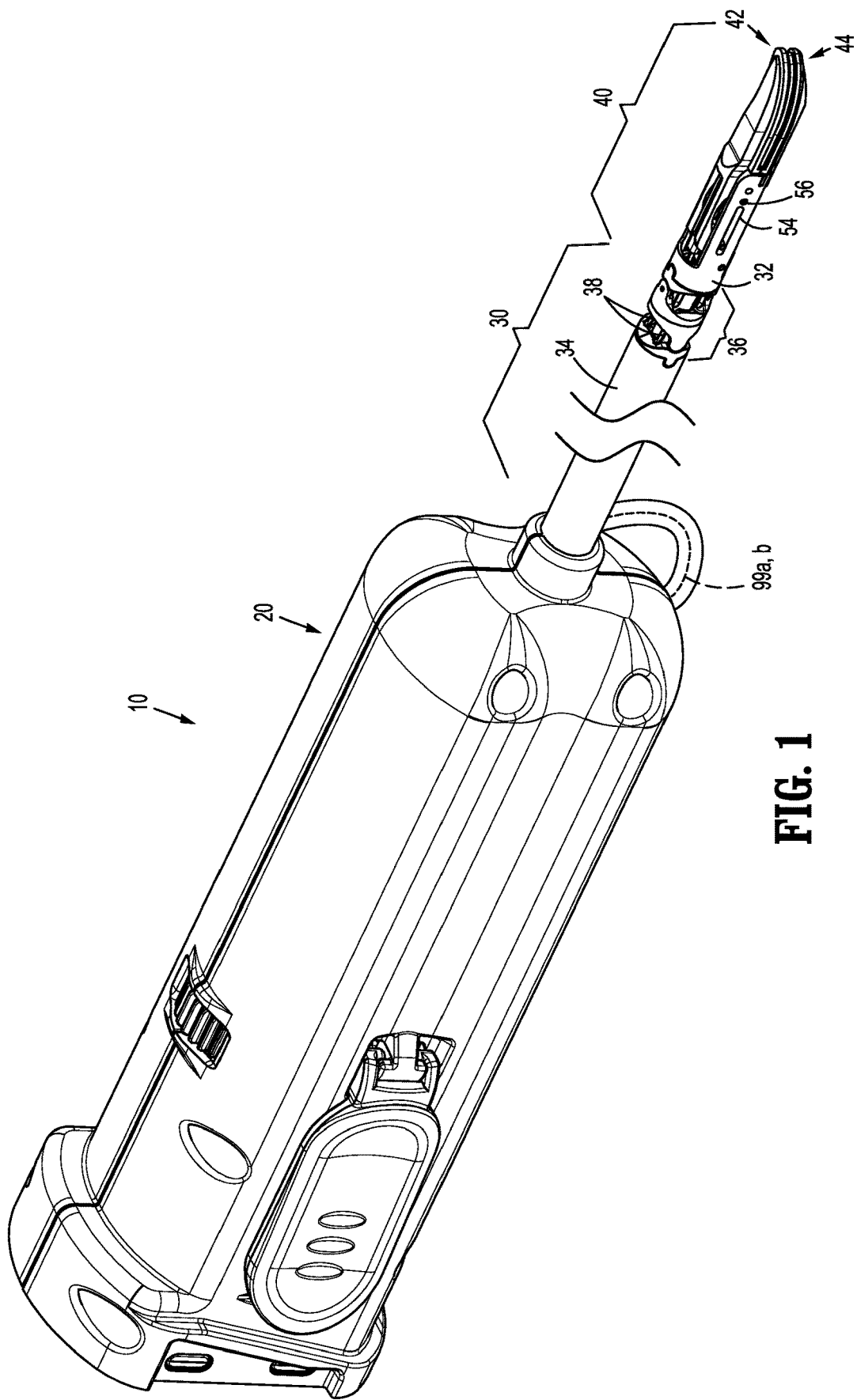
FIG. 1 is a perspective view of a surgical instrument provided in accordance with the present disclosure configured for mounting on a robotic arm of a robotic surgical system.
Figure 10:
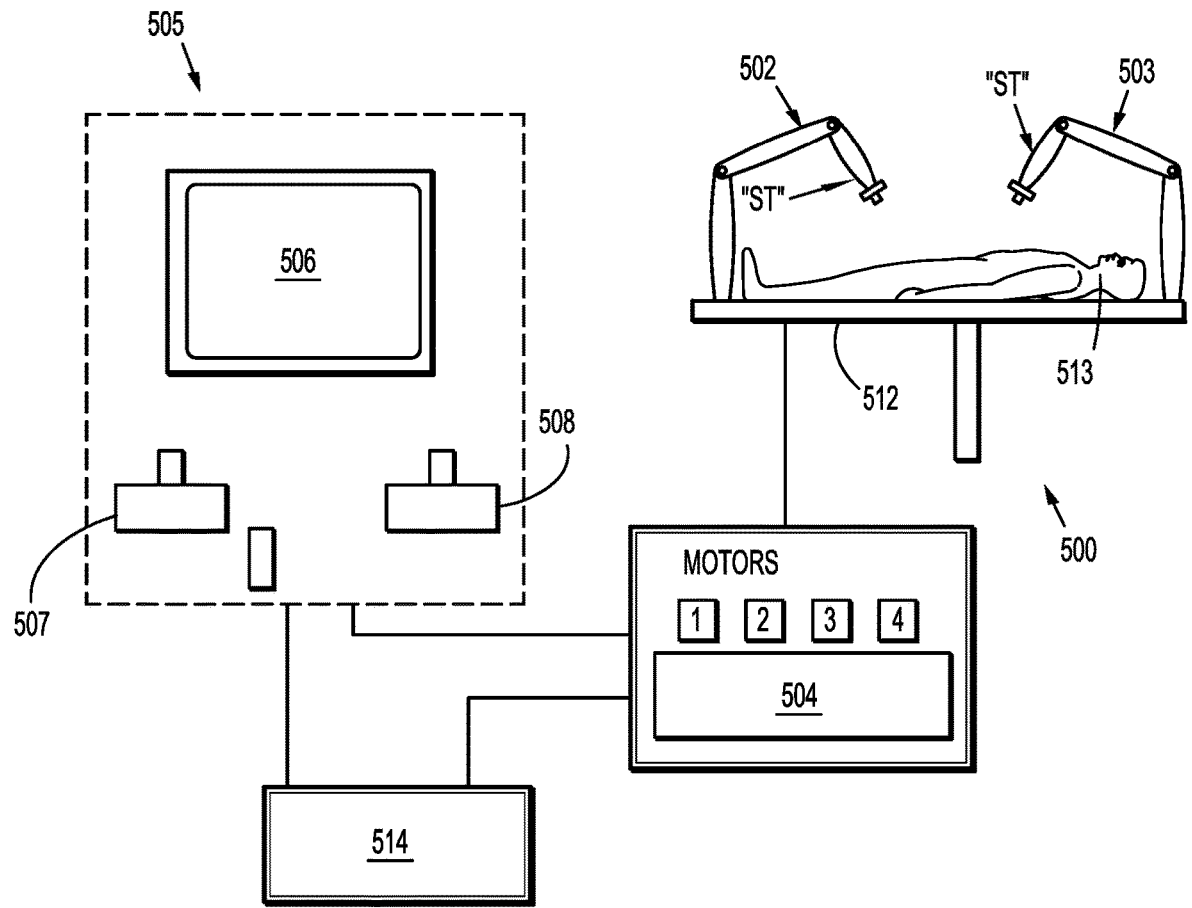
FIG. 10 is a schematic illustration of an exemplary robotic surgical system configured to releasably receive the surgical instrument of FIG. 1.

Referring to FIG. 1, a surgical instrument 10 provided in accordance with the present disclosure generally includes a housing 20, a shaft assembly 30 extending distally from housing 20, an end effector assembly 40 extending distally from shaft assembly 30, and an actuation assembly (not explicitly shown) disposed within housing 20 and operably associated with shaft assembly 30 and end effector assembly 40. Housing 20 of instrument 10 releasably engages with a robotic arm of a surgical system, e.g., robotic surgical system 500 (FIG. 10). Instrument 10 is detailed herein as an articulating electrosurgical forceps configured for use with a robotic surgical system, e.g., robotic surgical system 500 (FIG. 10). However, the aspects and features of instrument 10 provided in accordance with the present disclosure, detailed below, are equally applicable for use with other suitable surgical instruments and/or in other suitable surgical systems.

Shaft assembly 30 of instrument 10 includes a distal segment, such as, for example, a collar or clevis 32, a proximal segment 34, and an articulating section 36 disposed between the distal and proximal segments 32, 34. In aspects, the clevis 32 may alternatively form part of the end effector assembly 40. Articulating section 36 includes one or more articulating components, e.g., links, joints, etc. A plurality of articulation cables 38, e.g., four (4) articulation cables, or other suitable actuators, extends through articulating section 36. More specifically, articulation cables 38 are operably coupled to clevis 32 of shaft assembly 30 at the distal ends thereof and extend proximally from clevis 32 of shaft assembly 30, through articulating section 36 of shaft assembly 30 and proximal segment 34 of shaft assembly 30, and into housing 20, wherein articulation cables 38 operably couple with an articulation assembly (not explicitly shown) of the actuation assembly to enable selective articulation of clevis 32 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated.

Figure 6:
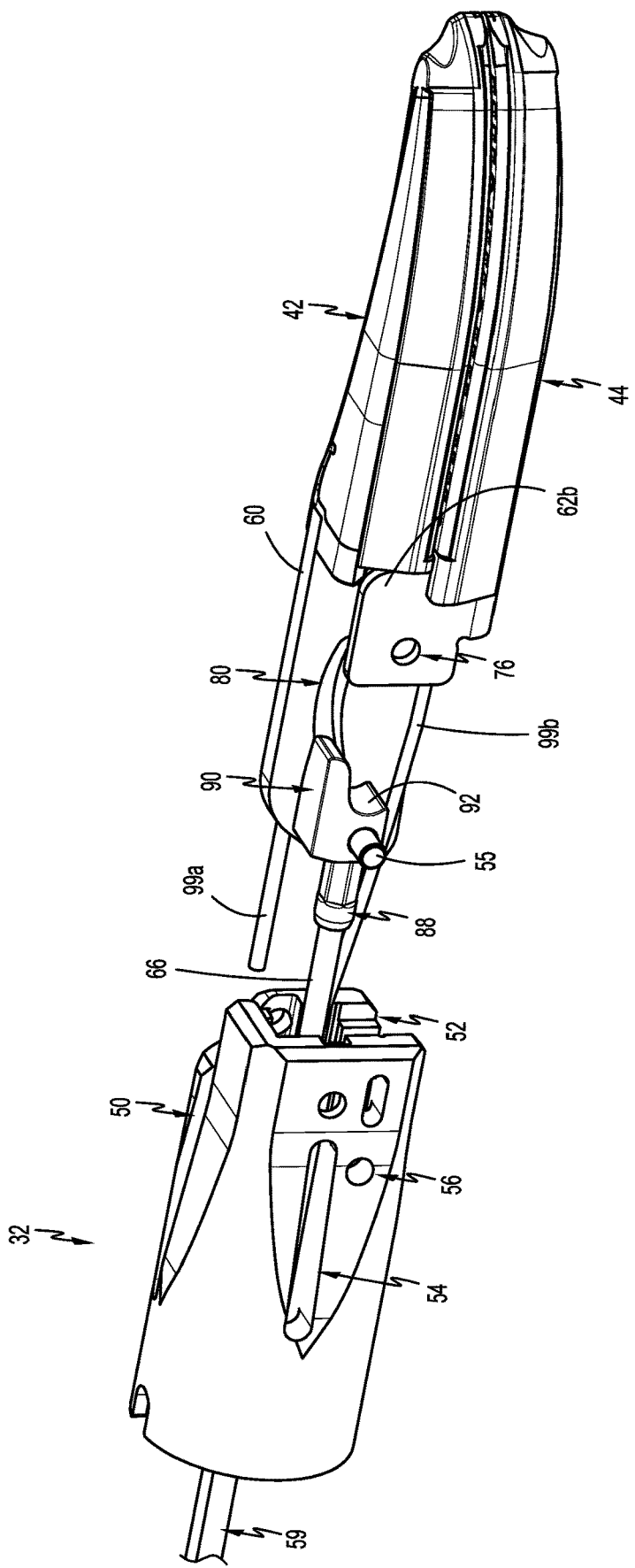
FIG. 6 is a side perspective view of the first and second jaw members and a cam bar of the end effector assembly of FIG. 2 with a clevis shown separated from the jaw members.
Figure 7:
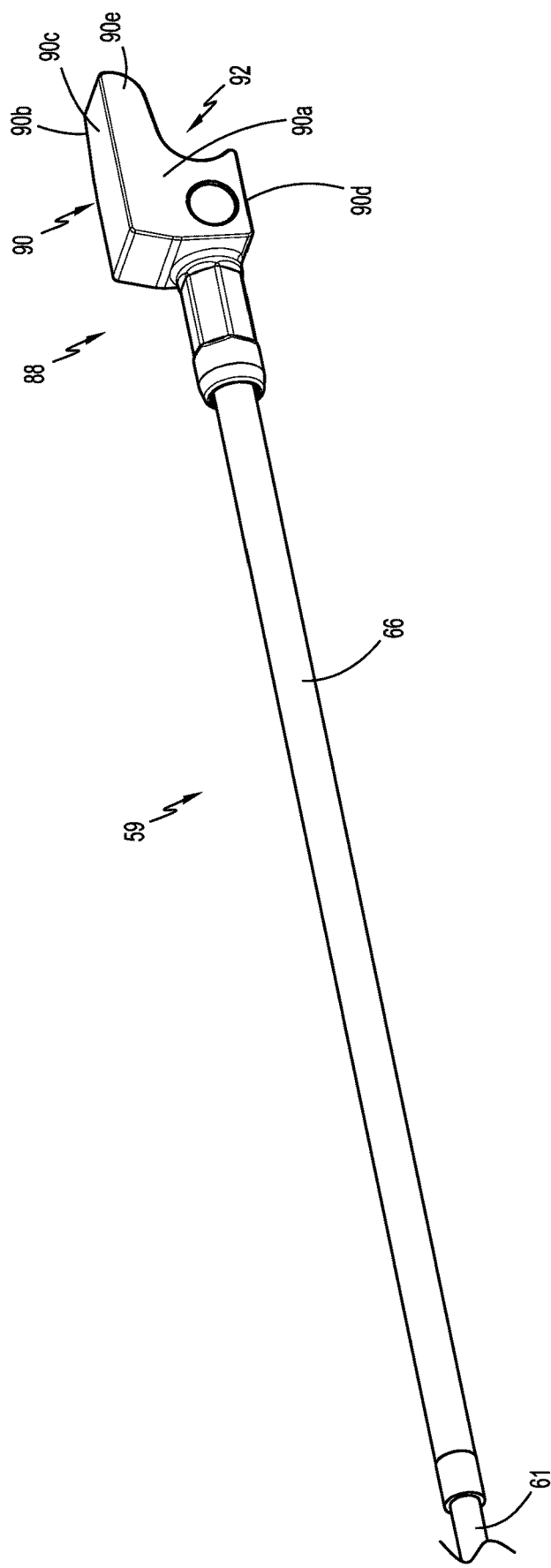
FIG. 7 is a perspective view illustrating the cam bar of FIG. 6.
Figure 8:
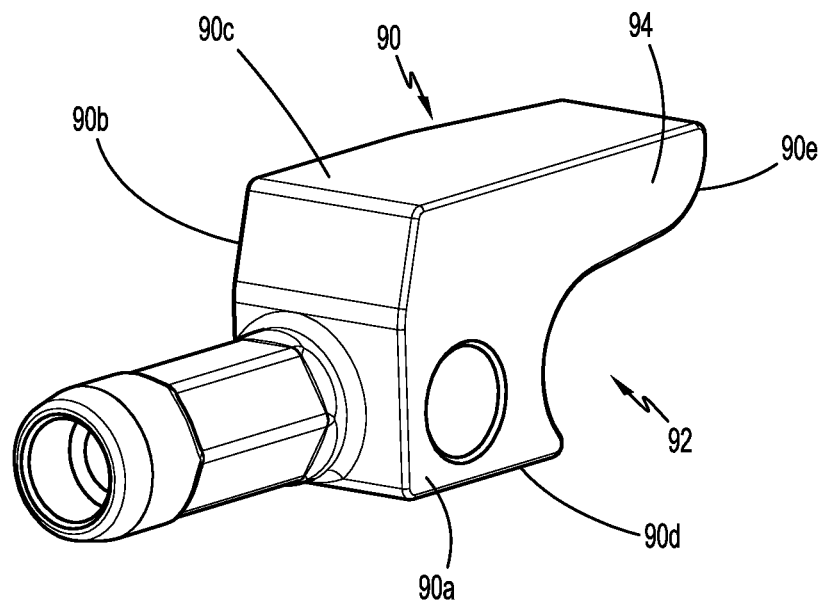
FIG. 8 is a perspective view illustrating a cam block of the cam bar of FIG. 7.
Figure 9:
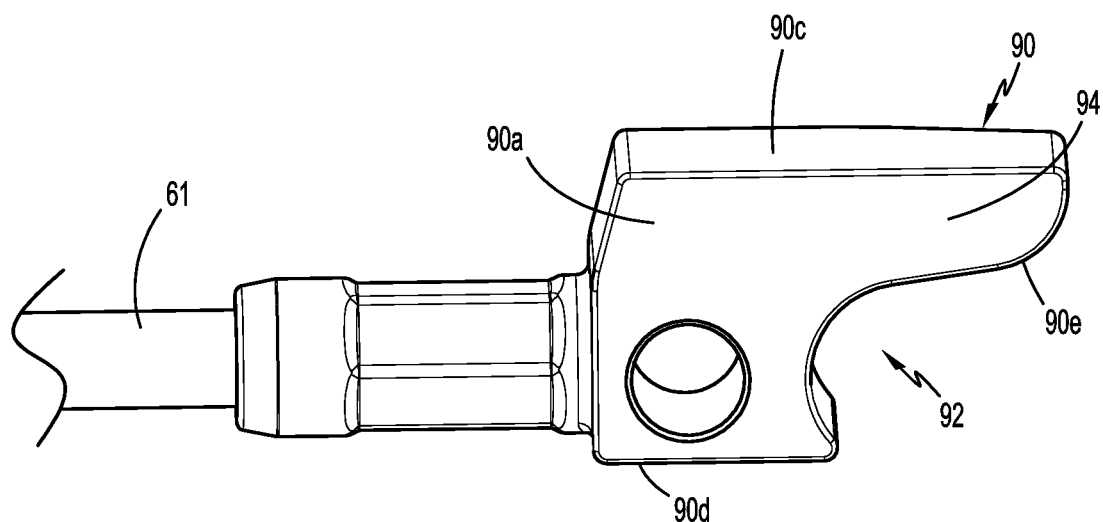
FIG. 9 is another perspective view illustrating the cam block of FIG. 7.

With reference to FIGS. 2, 3, and 6, clevis 32 includes first and second opposing upper and lower walls 32a, 32b and first and second opposing side walls 32c, 32d. Each of the upper and lower walls 32a, 32b defines an elongate cutout or slot 50, 52 (FIG. 6) that extends proximally from a distal end of the clevis 32 and partially through the length of the clevis 32. The elongate slots 50, 52 are configured for receipt of a proximal flange portion 60 of a first jaw member 42 of end effector assembly 40, as will be described in further detail below. At least the first side wall 32c defines a linear slot 54 that extends transversely through a thickness of the first side wall 32c. The linear slot 54 is configured for slidable receipt of a cam pin 55 of a cam bar 59 to guide and support cam bar 59 as cam bar 59 translates between proximal and distal positions relative to clevis 32. At least the first side wall 32c of clevis 32 defines an opening 56 therein that is disposed distally of and aligned with linear slot 54. Opening 56 in first side wall 32c is configured for receipt of a pivot pin 58 that secures first and second jaw members 42, 44 to clevis 32.

With reference to FIGS. 2-6, as mentioned above, end effector assembly 40 includes first and second jaw members 42, 44, respectively. In aspects, clevis 32 may also be considered a component of end effector assembly 40. Each jaw member 42, 44 includes a proximal flange portion 60, 62 and a distal body portion 64, 66, respectively. Distal body portions 64, 66 define opposed tissue-contacting surfaces 70, 72, respectively. Tissue-contacting surfaces 70, 72 of jaw members 42, 44, respectively, are at least partially formed from an electrically conductive material and are energizable to different potentials to enable the conduction of electrical energy through tissue grasped therebetween, although tissue-contacting surfaces 70, 72 may alternatively be configured to supply any suitable energy, e.g., thermal, microwave, light, ultrasonic, etc., through tissue grasped therebetween for energy-based tissue treatment. Instrument 10 defines a conductive pathway (not shown) through housing 20 and shaft assembly 30 to end effector assembly 40 that may include electric lead wires 99a, 99b (FIGS. 1 and 6), contacts, and/or electrically-conductive components to enable electrical connection of tissue-contacting surfaces 70, 72 of jaw members 42, 44, respectively, to an energy source (not shown), e.g., an electrosurgical generator via an electrosurgical cable extending therebetween, for supplying energy to tissue-contacting surfaces 70, 72 to treat, e.g., seal, tissue grasped between tissue-contacting surfaces 70, 72.

With reference to FIGS. 4-6, tissue-contacting surfaces 70, 72 each define a longitudinally-extending knife channel 74 (only knife channel 74 of second jaw member 44 is explicitly shown, FIG. 4). A knife assembly 78 is provided that includes a knife rod 78a and a knife blade 78b fixed to or otherwise coupled to a distal end of knife rod 78a. The knife rod 78a extends from housing 20 through shaft assembly 30 to end effector assembly 40. Knife blade 78b is disposed within end effector assembly 40 between jaw members 42, 44 and is provided to enable cutting of tissue grasped between tissue-contacting surfaces 70, 72 of jaw members 42, 44, respectively. Knife rod 78a is operably coupled to a knife drive assembly (not explicitly shown) of the actuation assembly of the housing 20 to enable selective actuation thereof to, in turn, reciprocate the knife blade 78b between jaw members 42, 44 to cut tissue grasped between tissue-contacting surfaces 70, 72.

Proximal flange portions 60, 62 of respective first and second jaw members 42, 44 are pivotably coupled to one another about pivot pin 58 (FIG. 3). For example, each of proximal flange portions 60, 62 of first and second jaw members 42, 44 defines a pin hole 76 (only pin hole of proximal flange portion 62 is explicitly shown, FIGS. 4-6) transversely therethrough in which pivot pin 58 is received. Further, as mentioned above, pivot pin 58 extends through pin holes 56 in clevis 32 such that first and second jaw members 42, 44 are axially restrained to clevis 32 while being permitted to rotate or pivot relative to clevis 32. Proximal flange portion 60 of first jaw member 42 may have a plate-like, rectangular configuration and defines an angled or curved cam slot 80 extending along a length thereof. The cam slot 80 is configured for receipt of cam pin 55 of cam bar 59.

Proximal flange portion 62 of second jaw member 44 may include a pair of first and second proximal flange portions 62a, 62b that are laterally spaced from one another to define a gap 82 therebetween. The proximal flange portion 60 of first jaw member 42 is received in the gap 82. Second jaw member 44 may further include a knife guide feature 84, such as, for example, a protuberance, supported on a proximal end of the distal body portion 66 of the second jaw member 44. The knife guide feature 84 protrudes toward the first jaw member 42 and defines a slot 86 having the knife blade 78b received therein when the knife blade 78b is in a proximal, pre-deployed position. As such, knife blade 78b is safely concealed within knife guide feature 84 when in the proximal position. Second jaw member 44 may further be secured to clevis 32, e.g., via welding of proximal flange portion 62 to clevis 32, or in any other suitable manner. Opposed slots 33 defined within side walls 32c, 32d (only slot 33 of side wall 32c is shown), for example, may provide access to facilitate welding proximal flange portions 62 to clevis 32, although other configurations are also contemplated.

With reference to FIGS. 6-9, cam bar 59 of end effector assembly 40 generally includes a jaw cable 61, and a distal end portion or cam block assembly 88 fixed to a distal end of cable 61. Cable 61 may be flexible to allow for translation of cam bar 59 through articulation section 36 (FIG. 1) without inhibiting articulation of articulation section 36. The cable 61 may be enshrouded with a lumen guide tube 66 fabricated from nickel titanium. However, other suitable materials are contemplated for lumen guide tube 66. Cable 61 of cam bar 59 extends proximally from end effector assembly 40 through shaft assembly 30 and into housing 20 wherein cable 61 is operably coupled with a jaw drive assembly (not explicitly shown) of the actuation assembly of housing 20 to enable selective actuation of end effector assembly 40 to grasp tissue therebetween and apply a closure force within an appropriate jaw closure force range.

Cam block assembly 88 of cam bar 59 includes a cam block 90, and the cam pin 55 extending outwardly from opposing lateral sides 90a, 90b of cam block 90. Cam block 90 may have a generally rectangular configuration and include first and second opposing lateral sides 90a, 90b and upper and lower opposing surfaces 90c, 90d. In aspects, each of the lateral sides 90a, 90b and upper and lower surfaces 90c, 90d may be planar. In aspects, cam block 90 may assume any suitable shape, such as, for example, cylindrical or the like. Lateral sides 90a, 90b and upper and lower surfaces 90c, 90d of cam block 90 are supported and guided by internal structures, e.g., complementary structures, within clevis 32 as cam bar 59 translates between proximal and distal positions to transition the end effector assembly 40 between the respective open and closed states.

The cam block 90 has a distal-facing surface 90e that extends between the upper and lower surfaces 90c, 90d. The distal-facing surface 90e defines a cutout 92 formed therein configured to receive the pivot pin 58 (FIG. 3) when the cam bar 59 is in the distal or deployed position. The cutout 92 may have an annular shape and provides cam block 90 with a distal extension 94 that passes distally of and above pivot pin 58 when cam bar 59 is in the distal position. The cutout 92, therefore, allows the full distal translation of the cam bar 59 without interference from the pivot pin 58 while allowing for cam block 90 to maintain an elongated configuration that ensures sufficient capture within or surface contact between cam block 90 and the internal structures within clevis 32, thus inhibiting cam block 90 from rotating, bending, breaking, or otherwise failing to function properly. In aspects, cutout 92 may assume other suitable shapes, such as, for example, square or v-shaped.

A first end of cam pin 55 of cam block assembly 88 is received in linear cam slot 54 of clevis 32 to guide and support a linear movement of cam bar 59, and a second end of cam pin 55 (not explicitly shown) is received in angled cam slot 80 of proximal flange portion 60 of first jaw member 42. Cam slot 80 in proximal flange portion 60 of first jaw member 42 is shaped such that retraction (e.g., proximal translation) of cam bar 59 relative to proximal flange portion 60 from a distal position to a proximal position causes the cam pin 55 to ride proximally through cam slot 80 and drive jaw member 42 to pivot toward second jaw member 44 to transition end effector assembly 40 from a spaced-apart position (e.g., an open position of end effector assembly 40) to an approximated position (e.g. a closed position of end effector assembly 40) for grasping tissue between tissue-contacting surfaces 70, 72. Similarly, advancement (e.g., distal translation) of cam bar 59 relative to proximal flange portion 60 causes cam pin 55 to ride distally through cam slot 80 and drive first jaw member 42 to pivot away from second jaw member 44 to transition end effector assembly 40 from the closed state to the open state. As an alternative to this unilateral configuration, a bilateral configuration may be provided whereby both jaw members 42, 44 are pivotable relative to one another and clevis 32 of shaft assembly 30. Additionally or alternatively, cam bar 59 may be moved distally to transition end effector assembly 40 to the approximated position and proximally to transition end effector assembly 40 to the spaced-apart position.

Turning to FIG. 10, robotic surgical system 500 is configured for use in accordance with the present disclosure. Aspects and features of robotic surgical system 500 not germane to the understanding of the present disclosure are omitted to avoid obscuring the aspects and features of the present disclosure in unnecessary detail.

Robotic surgical system 500 generally includes a plurality of robot arms 502, 503; a control device 504; and an operating console 505 coupled with control device 504. Operating console 505 may include a display device 506, which may be set up in particular to display three-dimensional images; and manual input devices 507, 508, by means of which a person, e.g., a surgeon, may be able to telemanipulate robot arms 502, 503 in a first operating mode. Robotic surgical system 500 may be configured for use on a patient 513 lying on a patient table 512 to be treated in a minimally invasive manner. Robotic surgical system 500 may further include a database 514, in particular coupled to control device 504, in which are stored, for example, preoperative data from patient 513 and/or anatomical atlases.

Each of the robot arms 502, 503 may include a plurality of members, which are connected through joints, and a mounted device which may be, for example, a surgical tool "ST." One or more of the surgical tools "ST" may be instrument 10 (FIG. 1), thus providing such functionality on a robotic surgical system 500.

Robot arms 502, 503 may be driven by electric drives, e.g., motors, connected to control device 504. Control device 504, e.g., a computer, may be configured to activate the motors, in particular by means of a computer program, in such a way that robot arms 502, 503, and, thus, their mounted surgical tools "ST" execute a desired movement and/or function according to a corresponding input from manual input devices 507, 508, respectively. Control device 504 may also be configured in such a way that it regulates the movement of robot arms 502, 503 and/or of the motors.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. An end effector assembly of a robotic surgical instrument, the end effector assembly comprising:
    a clevis;
    a first jaw member pivotably coupled to the clevis via a pivot pin, the first jaw member defining a cam slot;
    a second jaw member coupled to the clevis; and
    a cam bar having a distal end portion received within the clevis, the distal end portion of the cam bar including a cam block supporting a cam pin, the cam pin received in the cam slot defined in the first jaw member, the cam block defining an upper surface, a lower surface, a pair of lateral side surfaces, and a distally-facing surface extending continuously between the upper and lower surfaces and between the pair of lateral sides, the distally-facing surface defining a cutout forming a concavity in the distally-facing surface configured to receive the pivot pin, wherein the cam bar is configured to move the cam block through the clevis to thereby move the cam pin through the cam slot to pivot at least one of the first or second jaw members relative to the clevis between a closed state in which the first and second jaw members are closer to one another, and an open state in which the first and second jaw members are further apart from one another.

2. The end effector assembly according to claim 1, wherein the cam block is configured to move between a distal position, in which the first and second jaw members are in the open state, and a proximal position, in which the first and second jaw members are in the closed state.

3. The end effector assembly according to claim 2, wherein the pivot pin is configured to be received in the concavity of the distally-facing surface of the cam block when the cam block is in the distal position.

4. The end effector assembly according to claim 1, wherein the cam pin extends laterally outward from at least a first lateral side of the cam block.

5. The end effector assembly according to claim 1, wherein the clevis has a side wall defining a linear slot, the cam pin received in the linear slot.

6. The end effector assembly according to claim 5, wherein the first jaw member includes a distal body portion, and a proximal flange portion extending proximally from the distal body portion, the proximal flange portion defining the cam slot therein.

7. The end effector assembly according to claim 5, wherein the clevis defines an opening having the pivot pin received therein, the opening disposed distally of the linear slot.

8. The end effector assembly according to claim 1, wherein the cam block supports the cam pin at a position proximally-spaced from an entirety of the distally-facing surface.

9. The end effector assembly according to claim 1, wherein the cam pin is longitudinally fixed relative to the cam block.

10. The end effector assembly according to claim 1, wherein the cam bar includes a flexible cable.

11. A robotic surgical instrument, comprising:
    a housing configured to be operably coupled to a surgical robotic arm;
    a shaft assembly extending distally from the housing; and
    an end effector assembly including:
        a clevis coupled to a distal end portion of the shaft assembly and configured to articulate relative thereto;
        a first jaw member pivotably coupled to the clevis via a pivot pin, the first jaw member defining a cam slot;
        a second jaw member coupled to the clevis; and
        a cam bar having a distal end portion received within the clevis, the distal end portion of the cam bar including a cam block supporting a cam pin, the cam pin received in the cam slot defined in the first jaw member, the cam block having a distally-facing surface extending continuously between lateral side surfaces of the cam block and defining a cutout such that a first portion of the distally-facing surface protrudes further distally than a second portion of the distally-facing surface, the cutout forming a concavity in the distally-facing surface configured to receive the pivot pin, wherein the cam bar is configured to move the cam block through the clevis to thereby move the cam pin through the cam slot to pivot at least one of the first or second jaw members relative to the clevis between a closed state in which the first and second jaw members are closer to one another, and an open state in which the first and second jaw members are further apart from one another.

12. The robotic surgical instrument according to claim 11, wherein the cam block is configured to move between a distal position, in which the first and second jaw members are in the open state, and a proximal position, in which the first and second jaw members are in the closed state.

13. The robotic surgical instrument according to claim 12, wherein the pivot pin is configured to be received in the concavity of the cam block when the cam block is in the distal position.

14. The robotic surgical instrument according to claim 11, wherein the cam pin extends laterally outward from at least a first lateral side of the cam block.

15. The robotic surgical instrument according to claim 11, wherein the clevis has a side wall defining a linear slot, the cam pin of the cam bar received in the linear slot.

16. The robotic surgical instrument according to claim 15, wherein the first jaw member includes a distal body portion, and a proximal flange portion extending proximally from the distal body portion, the proximal flange portion defining the cam slot therein.

17. The robotic surgical instrument according to claim 15, wherein the clevis defines an opening having the pivot pin received therein, the opening disposed distally of the linear slot.

18. The robotic surgical instrument according to claim 11, wherein the cam block supports the cam pin at a position proximally-spaced from an entirety of the distally-facing surface.

19. The robotic surgical instrument according to claim 11, wherein the cam pin is longitudinally fixed relative to the cam block.

20. The robotic surgical instrument according to claim 11, wherein the cam bar includes a flexible cable.

* * * * *